US005597390A

United States Patent [19]
Loper

[11] Patent Number: 5,597,390
[45] Date of Patent: Jan. 28, 1997

[54] AMINE ESTER-CONTAINING ADDITIVES AND METHODS OF MAKING AND USING SAME

[75] Inventor: John T. Loper, Richmond, Va.

[73] Assignee: Ethyl Corporation, Richmond, Va.

[21] Appl. No.: 533,578

[22] Filed: Sep. 25, 1995

[51] Int. Cl.$^6$ ............................ C10L 1/22; C10M 133/04
[52] U.S. Cl. ............................. 44/391; 560/130; 560/138; 560/140; 560/144; 560/145; 560/146; 560/155; 560/169; 508/249; 508/263; 508/476; 544/87; 544/130; 546/190
[58] Field of Search ........................... 44/391; 560/130, 560/140, 144, 145, 155, 169; 252/51.5 R

[56] References Cited

U.S. PATENT DOCUMENTS

| | | | |
|---|---|---|---|
| 2,782,240 | 2/1957 | Hefner et al. | 568/608 |
| 2,841,479 | 7/1958 | Hefner et al. | 44/443 |
| 3,005,828 | 10/1961 | Baldridge | 44/391 |
| 3,144,311 | 8/1964 | Armstrong et al. | 44/340 |
| 3,146,203 | 11/1964 | Frew | 44/341 |
| 3,457,286 | 7/1969 | Dexter et al. | 44/391 |
| 3,920,729 | 11/1975 | Sagawa et al. | 44/391 |
| 3,944,397 | 3/1976 | Gardiner et al. | 44/425 |
| 4,198,306 | 4/1980 | Lewis | 252/51.5 R |
| 4,210,425 | 7/1980 | Cummings | 44/399 |
| 4,247,301 | 1/1981 | Honnen | 44/334 |
| 4,288,612 | 9/1981 | Lewis et al. | 560/159 |
| 4,329,240 | 5/1982 | Lilburn | 252/51.5 A |
| 4,568,358 | 2/1986 | Courtney | 44/387 |
| 4,600,409 | 7/1986 | Campbell | 44/387 |
| 4,695,291 | 9/1987 | Plavac | 44/387 |
| 4,869,728 | 9/1989 | Sung | 44/419 |
| 4,881,945 | 11/1989 | Buckley, III | 44/387 |
| 4,944,770 | 7/1990 | Sung | 44/415 |
| 4,997,456 | 3/1991 | Malfer | 44/347 |
| 5,055,607 | 10/1991 | Buckley,III | 560/158 |
| 5,122,616 | 6/1992 | Malfer | 44/347 |
| 5,131,921 | 7/1992 | Sung et al. | 44/391 |
| 5,197,997 | 3/1993 | Mozdzen et al. | 44/386 |
| 5,234,612 | 8/1993 | Carlisle | 252/51.5 R |
| 5,360,460 | 11/1994 | Mozdezen et al. | 44/386 |
| 5,387,266 | 2/1995 | Loper | 44/415 |
| 5,399,277 | 3/1995 | Patil | 252/51.5 R |
| 5,468,263 | 11/1995 | Chung et al. | 44/391 |
| 5,482,523 | 1/1996 | Cherpeck | 44/391 |

OTHER PUBLICATIONS

Encyclopedia of Polymer Science and Technology; Plastics, Resins, Rubbers, Fibers; vol. 6 (1967) pp. 108–112. (Month N/A).

*Primary Examiner*—Ellen M. McAvoy
*Attorney, Agent, or Firm*—Dennis H. Rainear

[57] ABSTRACT

A di- or tri-ester polyether unsaturated acid amine reaction product effective as a fuel additive for reducing intake valve deposits and octane requirement increase, as well as controlling combustion chamber deposits, in gasoline engines is disclosed together with fuel compositions and methods of making and using the same. Also disclosed are compositions and methods for dispersing deposits in lubricating oil products.

32 Claims, No Drawings

AMINE ESTER-CONTAINING ADDITIVES AND METHODS OF MAKING AND USING SAME

BACKGROUND OF THE INVENTION

1. Field of the Invention

The present invention relates to a novel class of compounds having utility as fuel additives, lubricant additives, fuel compositions, lubricant compositions and methods of making and using such additives. In particular, the present invention relates to a multi-functional amine-containing additive effective at reducing intake valve deposits and octane requirement increase, as well as controlling combustion chamber deposits, in gasoline engines, and methods of making and using the additive.

2. Background Discussion

Considerable effort has been expended to develop chemical products as fuel detergents or "deposit control" additives. Oil-soluble detergent-dispersants have also been developed to control deposit and varnish formation, and to keep sludge and other solid matter, such as oxidized base oil, in suspension in lubricating oil. Fuel detergents, when added to hydrocarbon fuels employed in internal combustion engines, effectively reduce deposit formation which ordinarily occurs in carburetor ports, throttle bodies, venturies, intake ports and intake valves. The reduction of these deposit levels has resulted in increased engine efficiency and a reduction in the level of hydrocarbon and carbon monoxide emissions.

However, with the advent of automobile engines that require the use of non-leaded gasolines (to prevent disablement of catalytic converters used to reduce emissions), it has been difficult to provide gasoline of high enough octane to prevent knocking and the concomitant damage which it causes. The difficulty is caused by octane requirement increase, herein called "ORI", which is due to deposits formed in the combustion chamber while the engine is operating on commercial gasoline.

Each engine, when new, requires a certain minimum octane fuel to operate satisfactorily without pinging and/or knocking. As the engine is operated on any gasoline, this minimum octane requirement increases. In most cases, if the engine is operated on the same fuel for a prolonged period it will reach equilibrium. This is apparently caused by an amount of deposits in the combustion chamber. Equilibrium is typically reached after 5000 to 15,000 miles of automobile operation.

ORI measured in particular engines with commercial gasolines will, at equilibrium, vary from 5 or 6 octane units to as high as 12 or 15 units, depending upon the gasoline compositions, engine design and type of operation. The seriousness of the problem is thus apparent. A typical current model year or older automobile with a research octane requirement of 85 when new may after a few months of operation require 97 research octane gasoline for proper operation, and little unleaded gasoline of that octane is available. The ORI problem exists in some degree with engines operated on leaded fuels. U.S. Pat. Nos. 3,144,311 and 3,146,203 disclose lead-containing fuel compositions having reduced ORI properties.

Many experts, believe the ORI problem, while present with leaded gasolines, is much more serious with unleaded fuel because of the different nature of the deposits formed with the respective fuels, the size of the increase, and because of the lesser availability of high-octane non-leaded fuels. This problem is compounded by the fact that the most common means of enhancing the octane of unleaded gasoline, increasing its aromatic content, also appears to increase the eventual octane requirement of the engine. Furthermore, some of the presently used nitrogen-containing deposit control additives with mineral oil or polymer carriers appear to contribute significantly to the ORI of engines operated on unleaded fuel.

Thus, it would be highly desirable to provide fuel compositions which contain deposit control additives which effectively control deposits in intake systems of engines, i.e., intake valve deposits (IVD), operated with fuels containing them, but do not contribute to the combustion chamber deposits (CCD) which cause octane requirement increase (ORI). It would also be desirable to provide lubricating oil compositions which contain deposit control additives which effectively control deposits in lubricating systems of engines.

SUMMARY OF THE INVENTION

The invention is directed to a novel class of compounds having particular utility as additives for distillate fuel, so as to reduce IVD and ORI as well as control CCD.

The invention is also directed to a novel class of compounds having particular utility as dispersants for lubricating oil.

The invention is also directed to a method of operating an internal combustion engine with spark ignition in a manner to reduce IVD and ORI as well as control CCD.

This invention is also directed to a distillate fuel composition comprising the compounds of the present invention.

The invention is also directed to a method of operating an internal combustion engine with spark ignition in a manner to reduce lubrication system deposits.

This invention is also directed to a lubricant composition comprising the compounds of the present invention.

The invention is also directed to a method of making the compounds of the present invention by a Michael reaction.

In particular, the present invention provides a single agent effective at reducing IVD and ORI as well as controlling CCD in gasoline engines. The agent can be synthesized by a Michael reaction of an amine and an unsaturated di- or tri-ester. The unsaturated di- or tri-ester contains a hydrocarbyl diol or triol with at least two poly(oxyalkylene) chains that has been esterified with a "reactive" carbonyl moiety. Such "reactive" carbonyl moieties are defined as a molecule where the chemical reaction with the polyalkylene chain will occur at the carbonyl site, not its unsaturated, i.e., olefin, site. Reactive unsaturated carbonyls include unsaturated monocarboxylic acid, ester, acid halide, lactone or anhydride.

DETAILED DESCRIPTION OF THE PREFERRED EMBODIMENTS

The present invention is directed to a class of compounds of Formula I:

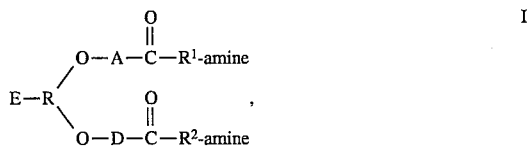

wherein E is selected from the group consisting of H and a moiety of Formula I(a):

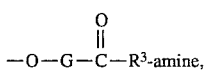

$$\text{I(a)}$$

wherein R is a hydrocarbyl group, $R^1$, $R^2$ and $R^3$ each independently represent an alkylene having from 2 to 5 carbon atoms, and A, D and G are as defined below.

Preferably, E is H such that the present invention is directed to a class of compounds of Formula II:

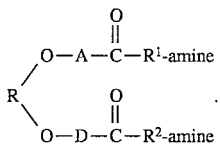

II

In Formula II, the substituents A, D, $R^1$ and $R^2$ have the same meaning as in Formula I above.

Hydrocarbyl is defined in connection with this specification and claims as a hydrocarbyl residue of a diol or triol which is an organic radical, composed of carbon and hydrogen, which may be aliphatic, alicyclic, aromatic or combinations thereof, e.g., aralkyl. Typically, the hydrocarbyl R is a diol which is substituted or unsubstituted. Preferably, the hydrocarbyl group is aromatic, most preferably aromatics having bis-functionality. The following are exemplary of the hydrocarbyls represented by R:

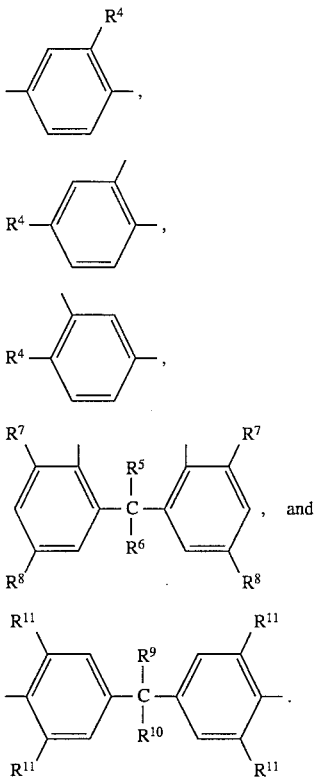

In Formula III, IV and V, $R^4$ is selected from the group consisting of H and $C_{1-60}$ alkyls. Preferably, $R^4$ is H.

In Formula VI, $R^5$ and $R^6$ may be the same or different and are selected from the group consisting of H and $C_{1-30}$ alkyls. Thus, an embodiment of Formula VI includes having $R^5$ as H and $R^6$ as a $C_{1-30}$ alkyl. Preferably, $R^5$ and $R^6$ may be the same or different and are selected from the group consisting of H and $C_{1-6}$ alkyls. More preferably, $R^5$ and $R^6$ are the same or different and are selected from the group consisting of H and $CH_3$. Each $R^7$ and $R^8$ may be the same or different and is selected from the group consisting of H and $C_{1-60}$ alkyls. Preferably, each $R^7$ and $R^8$ may be the same or different and is selected from the group consisting of H and $C_{1-2}$ alkyls. Most preferably, each $R^7$ is H.

In Formula VII, $R^9$ and $R^{10}$ may be the same or different and are selected from the group consisting of H and $C_{1-30}$ alkyls. Preferably, $R^9$ and $R^{10}$ may be the same or different and are selected from the group consisting of H and $C_{1-6}$ alkyls. More preferably, $R^9$ and $R^{10}$ are the same or different and are selected from the group consisting of H and $CH_3$. Each $R^{11}$ may be the same or different and is selected from the group consisting of H and $C_{1-60}$ alkyls. Preferably, each $R^{11}$ may be the same or different and is selected from the group consisting of H and $C_{1-6}$ alkyls. Most preferably, $R^9$ and $R^{10}$ are methyl radicals and $R^{11}$ is selected from the group consisting of H and t-butyl.

In the present description of the present invention, the term alkyls includes linear alkyls, e.g., n-butyl, and branched alkyls, e.g., tert-butyl.

Moieties A, D and G contain repeating units which repeat according to an integer x, y and z, respectively, may be the same or different, and each represent an oxyalkylene group of Formula VIII:

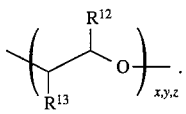

VIII $R^{12}$ and $R^{13}$ may be the same or different and each represent a member of the group consisting of H, $CH_3$ and $C_2H_5$. Preferably, $R^{12}$ represents a member of the group consisting of H, $CH_3$ and $C_2H_5$. Also, $R^{13}$ preferably represents a member of the group consisting of H and $CH_3$.

The values of x, y and z are the same or different and each of x, y and z is an integer from 1 to 40. Preferably the sum of x and y is an integer from 8 to 40 when E of Formula I is H. Most preferably, the sum of x and y is an integer from 8 to 20 when E of Formula I is H.

The moiety of Formula VIII is provided by employing an epoxide reactant of Formula IX:

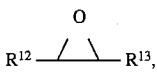

IX wherein $R^{12}$ and $R^{13}$ are as defined above. The moiety of Formula VIII may be formed by successively attaching alkoxy groups to the diol or triol by any known reaction mechanism as, for example described with regard to step XI below.

The second component employed in the preparation of an intermediate reaction product is carboxylic acid represented by the Formula X:

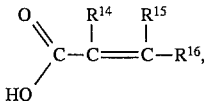

X in which $R^{14}$, $R^{15}$ and $R^{16}$ independently represent hydrogen or a methyl radical. Acrylic acid, i.e., where $R^{14}$, $R^{15}$ and $R^{16}$ are hydrogen, and methacrylic acid, i.e., where $R^{14}$ is methyl and $R^{15}$ and $R^{16}$ are hydrogen, are preferred. Acrylic acid is most preferred.

The amines of Formula I are amine moieties which typically contain from 1 to 10 nitrogen atoms. The amine moieties can have a structure which is aliphatic, cycloaliphatic, aromatic, heterocyclic, aliphatic and cycloaliphatic, aliphatic and aromatic, aliphatic and heterocyclic, cycloaliphatic and aromatic, cycloaliphatic and heterocyclic, or aromatic and heterocyclic. The amine moieties may be saturated or contain olefinic, acetylenic and/or aromatic unsaturation. Also, they may or may not contain other functional substituents, e.g., alkoxy substituents. The amine moieties are sterically unencumbered sufficiently to permit the below-described Michael reaction. Furthermore, one skilled in the art, given the teachings herein, would select amine moieties of appropriate molecular weight for the particular use as a fuel or lubricant additive. Preferably, the amine moieties are polyamines which contain from 2 to 10 nitrogen atoms. Also preferably, the amine moieties contain an average of up to 40 carbon atoms. The compounds of this invention can be formed from amine moieties having combinations of primary and secondary and/or tertiary amino groups. However, each amine moiety contains at least one primary or secondary amino group or is an ammonia moiety, i.e., —$NH_2$. Mixtures of suitable amines can be used, such as for example, commercial mixtures of straight chain, branched chain and cyclic ethylene polyamines having approximate overall compositions falling in the range corresponding to diethylene triamine to pentaethylene hexamine.

Particularly preferred amines include ethylene diamine (EDA); diethylene triamine (DETA); triethylene tetramine (TETA); alkyl etheramines, wherein the alkyl is $C_{1-30}$ hydrocarbon; amino ethyl ethanol amine (AEEA); dimethylaminopropylamine (DMAPA), i.e., $NH_2(CH_2)_3N(CH_3)_2$, or aminopropyl morpholine, i.e.,

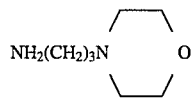

and aminoethyl piperadine (AEP), i.e.,

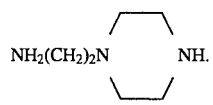

Suitable alkyl etheramines include those selected from the group consisting of $NH_2(CH_2)_3OR^{17}$ and $NH_2(CH_2)_3NH(CH_2)_3OR^{17}$, wherein $R^{17}$ is an alkyl having from 6 to 26 carbon atoms. Preferably, each alkyl etheramine is independently selected from the group consisting of $NH_2$—$(CH_2)_3$—NH—$(CH_2)_3$—$OC_{13}H_{27}$, $NH_2$—$(CH_2)_3$—NH—$(CH_2)_3$—$OC_{10}H_{21}$, $NH_2$—$(CH_2)_3$—$OC_{13}H_{27}$, and $NH_2$—$(CH_2)_3$—$OC_{10}H_{21}$.

Method for Making the Compounds of the Present Invention

In general, the compounds of the present invention are made by reacting an unsaturated ester with an amine by the Michael reaction.

In one embodiment, the unsaturated ester may be made by reacting a polyol, e.g., diol or triol, with epoxides, to form an alkyl polyether, followed by reacting the alkyl polyether with unsaturated carboxylic acid to form an unsaturated ester. The unsaturated ester is then reacted with an amine according to the Michael reaction.

The polyol and epoxides are combined and the epoxides polymerized, to form a hydrocarbyl ether polyoxyalkylene intermediate, as follows in step XI.

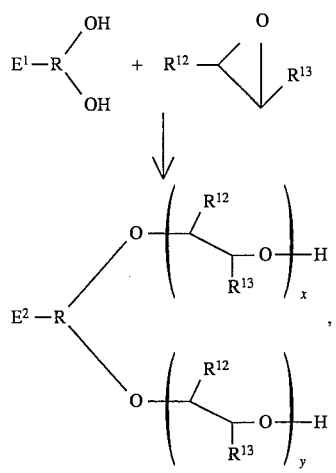

wherein $E^1$ is H or OH and $E^2$ is H or a moiety of Formula XI (a):

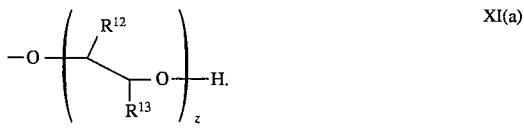

In step XI, poly(oxyalkylene) alcohol chains are attached to the diol or triol reactant, having the hydrocarbyl group R, by the addition of lower alkylene oxides, i.e., oxiranes, such as ethylene oxide, propylene oxide, the butylene oxides, or the pentylene oxides to a hydroxy group of the diol or triol reactant under polymerization conditions. Methods of production and properties of these polymers are disclosed in U.S. Pat. Nos. 2,841,479 and 2,782,240 and the "Encyclopedia of Polymer Science and Technology," Volume 6, pages 108–112 (1967) (Intersciences Publishers, division of John Wiley & Sons, Inc.) all of which are incorporated herein by reference. In the polymerization reaction, a single type of alkylene oxide may be employed, e.g., propylene oxide, in which case the product has homopolymer, e.g., poly(oxypropylene) alcohol, chains. However, copolymers are equally satisfactory and random copolymers are readily prepared by contacting the hydroxyl-containing compound with a mixture of alkylene oxides, such as a mixture of propylene oxide and butylene oxide, or a mixture of isomers of butylene oxide. Block copolymers of oxyalkylene units also provide satisfactory poly(oxyalkylene) polymers for the practice of the present invention. Random polymers are more easily prepared when the reactivities of the oxides are relatively equal. In certain cases, when ethylene oxide is copolymerized with other oxides, the higher reaction rate of ethylene oxide makes the preparation of random copolymers difficult. In either case, block copolymers can be prepared. Block copolymers are prepared by reacting the hydroxyl-containing compound with one alkylene oxide, then the others in any order, or repetitively, under polymerization conditions. A particular block copolymer has polymer chains prepared by polymerizing propylene oxide on suitable monohydroxy chains to form poly(oxypropylene) alcohol chains and then polymerizing butylene oxide on the poly(oxypropylene) alcohol chains.

In general the poly(oxyalkylene) polymer chain-containing compounds produced by step XI are mixtures of compounds having different polymer chain lengths. However, their properties closely approximate those of the compound represented by the average composition and molecular weight.

As shown in step XII, the hydrocarbyl ether polyoxyalkylene intermediate, e.g., diol- or triol-polyether, formed by the above reaction is then reacted with a reactive unsaturated carbonyl moiety, e.g., unsaturated monocarboxylic acid, to form di- or tri-ester in which the unsaturation is retained as follows:

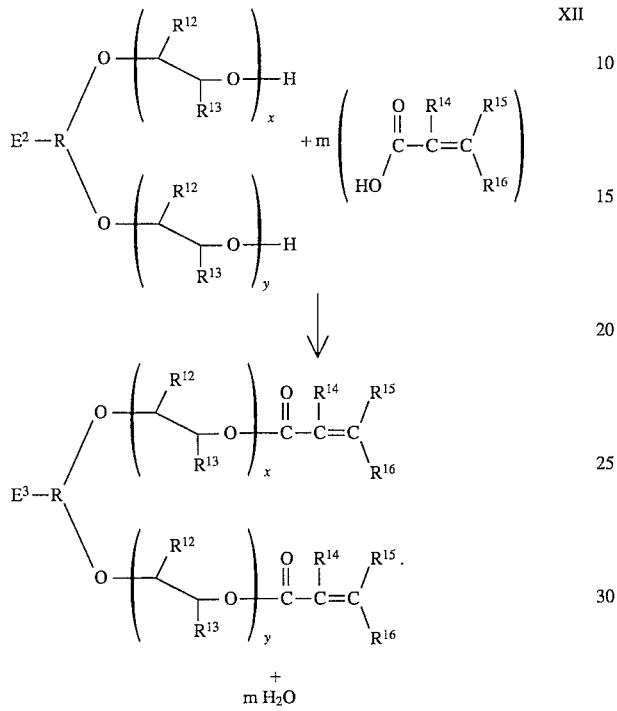

In step XII, $E^3$ is H or a moiety of Formula XII (a):

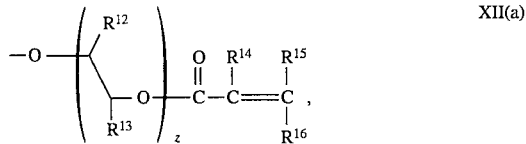

and m is 2, when $E^3$ is H, and m is 3 when $E^3$ is a compound of Formula XII(a).

While step XII is shown to employ monocarboxylic unsaturated acid, any reactive unsaturated carbonyl moiety, as discussed above, may be employed. Thus, in place of monocarboxylic unsaturated acid, moieties such as ester, acid halide, lactone or anhydride may be employed.

It is preferred to dissolve the reactants of step XII in an inert hydrocarbon and to employ a catalyst to speed up the reaction. Para-toluene sulfonic acid is a catalyst particularly effective for promoting the noted reaction. A small amount of an oxidation inhibitor, such as hydroquinone, is also useful for reducing the formation of undesirable byproducts, such as unsaturated monoacid polymerization products, for example, polyacrylic acid. It is preferred to effect the reaction at the reflux temperature of the solvent employed which, in the case of the solvent xylene is about 140° C. On completion of the preparation of the reaction product of step XII, the reaction mixture is cooled and the solvent is removed under reduced pressure.

Then, in step XIII, the unsaturated di- or tri-ester product of step XII is reacted with an amine, e.g., polyamine, by the Michael addition reaction as follows:

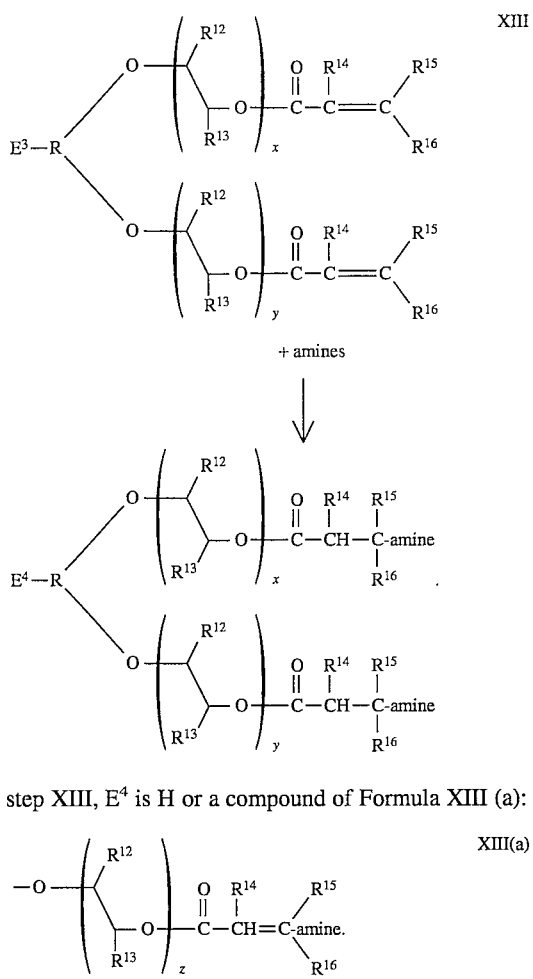

In step XIII, $E^4$ is H or a compound of Formula XIII (a):

In step XIII, the unsaturated di- or tri-ester is reacted by the Michael addition reaction with the amine to form one of the novel additives of the present invention. The Michael addition reaction is the addition of the ester, having olefinic unsaturation, to the amine to produce the product of step XIII. Typically, the Michael addition reaction employs from about 1 to 10, preferably from about 2 to 5 mols of amine per mol of ester. The reaction of Step XIII is conducted by admixing the reactants and maintaining them at a variety of temperatures and pressures, in the presence or absence of a solvent, and in the presence or absence of a catalyst. The reaction temperature ranges from about −10° C. up to a temperature below the decomposition temperature of the reactants and the reaction product. Typically, the reaction may be carried out at temperatures from about −10° C. to about 150° C. Preferably reaction temperature ranges from about 0° C. to about 100° C. A more preferred temperature range, where $E^4$ is a hydrogen atom and/or x plus y equals 8 to 30, is about 0° to about 25° C. Pressure may be atmospheric or vacuum.

As also stated above, the Michael addition for the amination reaction of step XIII may be conducted with or without the presence of a solvent. The solvent is generally employed whenever necessary to reduce the viscosity of the reactant mixture. These solvents should be stable and inert to the reactants and reaction product. Preferred solvents include liquid aliphatic or aromatic hydrocarbons, such as xylene or toluene. Depending on the temperature of the reaction, the particular ester used, the mol ratios and the particular amine, as well as the reactant concentrations, the reaction time may vary from less than 1 minute to 4 hours. After the reaction has been carried out for a sufficient length of time, the reaction mixture may be further diluted with hydrocarbon or hydrocarbon-alcohol media and extracted with water (preferably warm water to prevent emulsification), to free the product from any low-molecular-weight amine salts which have formed and any unreacted amines. The product may then be isolated by evaporation of the solvent. Depending on the particular application of the composition of this invention, the reaction may be carried out in the medium in which it may ultimately find use, e.g. polyether carriers or an oleophilic organic solvent or mixtures thereof and be formed at concentrations which provide a concentrate of a detergent composition. Thus, the final mixture may be in a form to be used directly for blending in fuel or lubricating oil compositions.

Measuring IVD, CCD and ORI

The effectiveness of a composition on IVD, CCD and ORI may be measured by a variety of procedures. Typical procedures are as follows.

IVD can be measured by employing a standard engine test procedure involving operating an engine for a given test period on a given test fuel. The engine at the start of the test would have a clean intake valve and upon completion of the test, the weight of the intake valve deposits is determined. The lower the weight of deposits, the more effective the composition.

CCD can be measured by employing a standard engine test procedure, involving operating an engine for a given test period on a given test fuel. The test would start with a clean combustion chamber and upon completion, the weight of the combustion chamber deposits is determined. The lower the weight of the deposits, the more effective the composition.

ORI can be measured by employing a standard engine test procedure, involving operating an engine for a given test period on a given test fuel. At the end of the test period, the engine is run with gasolines having varying levels of octane to determine when engine knock occurs. Knock can be detected by listening to the engine.

It is desirable that CCD is controlled, i.e., does not increase significantly, while IVD and ORI are decreased.

The present invention is further illustrated by the following non-limiting examples.

EXAMPLE 1

Preparation of Polyamine Diester 172 grams (0.25 mol) poly(alkylene glycol) Bisphenol A ethoxylate (4 EO/phenol) diacrylate (Aldrich Lot No. 05616 KF) was combined with 164.61 grams (0.5 mol) of DA-17, manufactured by Tomah Products Inc., Milton, Wis., which has an average composition of $NH_2—(CH_2)_3—NH—(CH_2)_3—OC_{13}H_{27}$ and 500 grams of toluene, and then stirred and heated to about 75° C. for about 3 hours. The mixture was then cooled and concentrated under vacuum. A product mixture having a net weight of 369.17 grams was recovered. This resulted in the following product of Formula XIV:

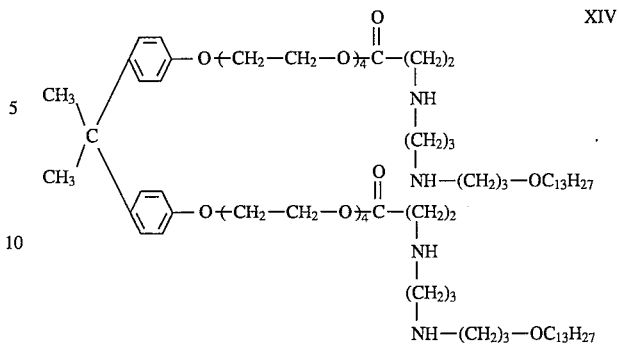

EXAMPLE 2

Engine Tests to Compare Fuels Containing the Present Additive with Other Additives The effectiveness of the compounds of this invention as detergents for fuels was demonstrated by comparative engine tests. These tests involved use of a standard engine test procedure for determining the amount of intake valve deposits formed when operating the engine for a test period of 150 hours on the test fuel. The base fuel used in these tests was an additive-free gasoline (Phillips J-42). Each test started with a clean intake valve and upon completion of the 150-hour test, the weight of the intake valve deposits was determined. Therefore, the lower the weight of deposits, the more effective the composition.

Three different additives were subjected to the foregoing test. The product of Example 1 was mixed with gasoline and tested at 100 lbs. per thousand barrels (PTB) in a single cylinder Briggs & Stratton engine. This mixture was labeled "Inventive Fuel A." Thus, Inventive Fuel A was composed of the base fuel containing 100 lbs. per thousand barrels of a compound of this invention formed as in Example 1. Inventive Fuel A was compared with Comparative Fuels A and B as well as an additive-free base fuel. Comparative Fuels A and B were composed of the base fuel containing 100 lbs. per thousand barrels of Comparative Compounds A and B, respectively.

Comparative Compound A was as follows:

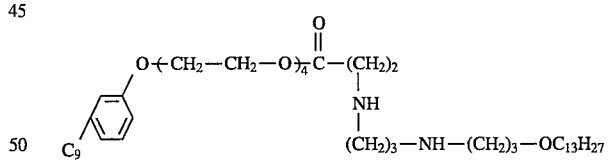

Comparative Compound B was as follows:

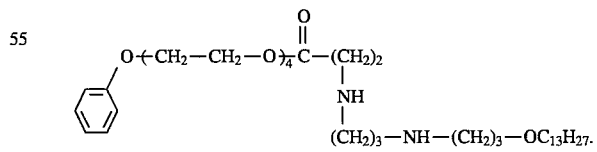

The resulting IVD deposits are listed on Table I. As Table I shows, Inventive Fuel A having two polyoxyalkylene polyamine chains, unexpectedly achieves a dramatic reduction of intake valve deposits as opposed to Comparative Fuels A and B, each having one polyoxyalkylene polyamine chain, or the Additive-Free Base Fuel. This reduction of intake valve deposits is important to increasing engine efficiency and reducing the level of hydrocarbon and carbon monoxide emissions from an engine.

TABLE I

| Fuel | IVD Deposits (mg.) |
| --- | --- |
| Inventive Fuel A | 183.3 |
| Comparative Fuel A | 597.7 |
| Comparative Fuel B | 433.8 |
| Additive-Free Base Fuel | 709 |

EXAMPLES 3–12

The procedure of Example 1 is repeated with various ingredients to make other compounds of the present invention. The poly(alkylene glycol) Bisphenol A ethoxylate (4 EO/phenol) diacrylate of Example 1 is replaced by another poly(oxyalkylene) unsaturated diester of Formula XII shown below, wherein $E^3$, $R^{14}$, $R^{15}$ and $R^{16}$ are each H, and R, $R^{12}$, $R^{13}$, x and y are as listed in Table II.

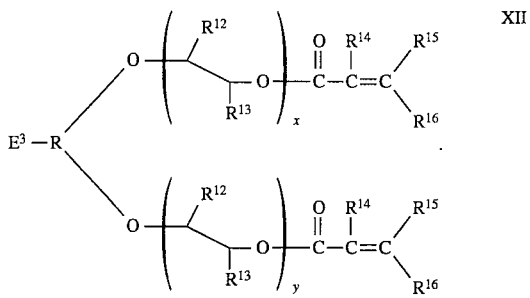
XII

Moreover, the unsaturated diester is reacted with an amine as listed in Table II.

TABLE II

| Ex-ample | R | Epoxide | | x plus y | Amines |
| | | $R^{12}$ | $R^{13}$ | | |
| --- | --- | --- | --- | --- | --- |
| 3 | Bisphenol A moiety | $CH_3$ | H | 10 | DA-17[3] |
| 4 | Bisphenol A moiety | $CH_3$ | H | 20 | DA-17[3] |
| 5 | Bisphenol A moiety | $C_2H_5$ | H | 10 | DMAPA[4] |
| 6 | Bisphenol A moiety | $C_2H_5$ | H | 20 | DMAPA[4] |
| 7 | Resorcinol moiety | $CH_2H_5$ | H | 20 | DA-17[3] |
| 8 | Hydroquinone | $C_2H_5$ | H | 20 | DA-17[3] |
| 9 | Hydrocarbyl A[1] | $CH_3$ | H | 20 | DA-17[3] |
| 10 | Hydrocarbyl A[1] | $C_2H_5$ | H | 10 | DMAPA[4] |
| 11 | Hydrocarbyl B[2] | $CH_3$ | H | 20 | DA-17[3] |
| 12 | Hydrocarbyl B[2] | $C_2H_5$ | H | 10 | DMAPA[4] |

[1]Compound of Formula VII, wherein $R^9$ and $R^{10}$ are H and $R^{11}$ is tertiary-butyl
[2]Compound of Formula VI, wherein $R^5$, $R^6$ and $R^7$ are H and $R^8$ is a $C_{12}$ alkyl
[3]Alkyl etheramine manufactured by Tomah Products Inc., Milton, Wisconsin, which has an average composition of $NH_2—(CH_2)_3—NH—(CH_2)_3—OC_{13}H_{27}$
[4]Dimethylaminopropylamine Employing the reactants of Examples 3–12 makes a wide variety of compounds for use as additives of the present invention.

The fuels of this invention will typically contain from about 100 ppm up to about 2% by weight of a compound of this invention. However, these levels are not limitations of the present invention. The fuels can be any distillate fuel such as gasoline (including so-called reformulated gasolines which contain oxygenates such as alcohols and/or ethers), diesel fuels, kerosenes, jet fuels, burner fuels, home heating oils, gas oils, and the like. It is preferred to employ the compounds of the present invention with gasoline.

The compounds of this invention may be employed as dispersants for use in natural and synthetic oils of lubricating viscosity. The lubricants of this invention will typically contain from about 0.5 to about 5% of a compound of this invention based on the weight of the finished lubricant or functional fluid composition. However, these levels are not limitations on the present invention.

The lubricating oils can be any animal, vegetable or mineral oil, for example petroleum oil to SAE 30, 40, or 50 lubricating oil grades, castor oil, fish oils or oxidized mineral oils. Alternatively the lubricating oil can be a synthetic ester lubricating oil. These esters include diesters such as di-octyl adipate, di-octyl sebacate, di-decyl glutarate and mixtures thereof. Alternatively, the synthetic ester can be a polyester such as that prepared by reacting polyhydric alcohols, such as trimethylolpropane and pentaerythritol, with monocarboxylic acids, such as butyric acid, to give the corresponding tri- and tetra esters. Also, complex esters may be used, such as those formed by esterification reactions between carboxylic acid, a glycol and an alcohol, or monocarboxylic acid.

The lubricants may further include conventional lubricant additives such as metal-containing detergents, antiwear agents, extreme pressure agents, corrosion inhibitors, foam inhibitors, friction modifiers, viscosity index improvers, pour point depressants, oxidation inhibitors, and the like.

This invention is susceptible to considerable variation in its practice. Accordingly, this invention is not intended to be limited by the specific exemplifications set forth hereinabove. Rather, this invention is intended to cover the subject matter within the spirit and scope of the appended claims and the permissible equivalents thereof.

I claim:

1. A compound of a Formula I:

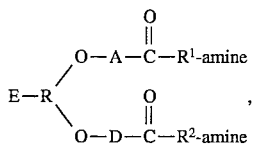
I wherein R is selected from a hydrocarbyl residue of a diol and a hydrocarbyl residue of a triol, A represents the moiety

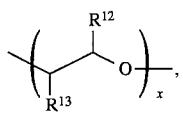
VIII(a)

D represents the moiety

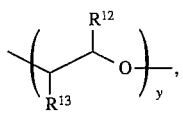
VIII(b)

E represents H or the moiety

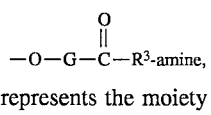
VIII(c)

G represents the moiety

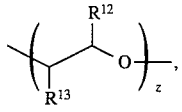
VIII(d)

wherein each amine comprises a member of the group consisting of ammonia, a primary amino group, a secondary amino group, and mixtures thereof, wherein $R^{12}$ and $R^{13}$, which may be the same or different, each independently represents a member of the group consisting of H, $CH_3$ and $C_2H_5$, x, y and z, which may be the same or different, are each an integer of from 1 to 40, $R^1$, $R^2$ and $R^3$, which may be the same or different, are each an alkylene having from 2 to 5 carbon atoms, and the amines being moieties which are the same or different, and each amine having from 1 to 10 nitrogen atoms, wherein each amine comprises at least one member of the group consisting of a primary amino group, a secondary amino group, and an ammonia moiety.

2. The compound of claim 1, wherein E is H.

3. The compound of claim 1, wherein the amines are moieties which are the same or different, and each amine has from 2 to 10 nitrogen atoms.

4. The compound of claim 1, wherein each amine moiety is independently selected from the group consisting of amines having at least one primary amino group, amines having at least one secondary amino group, and mixtures thereof.

5. The compound of claim 3, wherein each amine is independently a member selected from the group consisting of aliphatic amine, cycloaliphatic amine, aromatic amine, heterocyclic amine, aliphatic and cycloaliphatic amine, aliphatic and aromatic amine, aliphatic and heterocyclic amine, cycloaliphatic and aromatic amine, cycloaliphatic and heterocyclic amine, and aromatic and heterocyclic amine; wherein each amine is independently a member selected from the group consisting of saturated amine and unsaturated amine, wherein the unsaturation is selected from the group consisting of olefinic unsaturation, acetylenic unsaturation, aromatic unsaturation, and combinations of such unsaturation.

6. The compound of claim 1, wherein each amine is independently selected from the group consisting of ethylene diamine, diethylene triamine, triethylene tetramine, alkyl etheramine wherein alkyl is $C_1$–$C_{30}$ hydrocarbon, amino ethyl ethanol amine, dimethylaminopropylamine, aminopropyl morpholine, and aminoethyl piperadine.

7. The compound of claim 6, wherein each amine is independently the alkyl etheramine, wherein the alkyl is $C_1$–$C_{30}$ hydrocarbon.

8. The compound of claim 7, wherein each alkyl etheramine is independently selected from the group consisting of $NH_2(CH_2)_3OR^{17}$ and $NH_2(CH_2)_3NH(CH_2)_3OR^{17}$, wherein the alkyl is $R^{17}$ and $R^{17}$ has from 6 to 26 carbon atoms.

9. The compound of claim 5, wherein R is selected from the group consisting of:

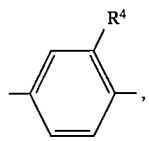

III

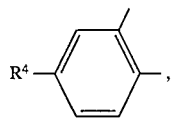

IV

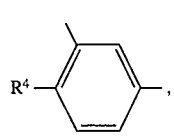

V

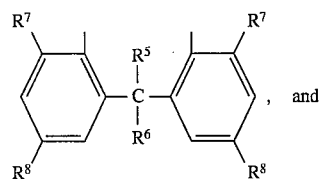

VI

, and

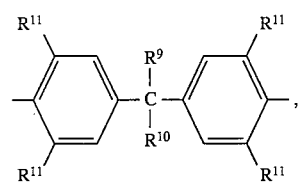

VII wherein $R^4$ is selected from the group consisting of H and $C_{1-60}$ alkyls;

$R^5$ and $R^6$ may be the same or different and are selected from the group consisting of H and $C_{1-30}$ alkyls;

each $R^7$ and $R^8$ may be the same or different and is selected from the group consisting of H and $C_{1-60}$ alkyls, $R^9$ and $R^{10}$ may be the same or different and is selected from the group consisting of H and $C_{1-30}$ alkyls, and each $R^{11}$ may be the same or different and is selected from the group consisting of H and $C_{1-60}$ alkyls.

10. The compound of claim 9, wherein each amine is independently selected from the group consisting of ethylene diamine, diethylene triamine, triethylene tetramine, alkyl etheramine wherein alkyl is $C_1$–$C_{30}$ hydrocarbon, amino ethyl ethanol amine, dimethylaminopropylamine, aminopropyl morpholine, and aminoethyl piperadine.

11. The compound of claim 9, wherein R is selected from the group consisting of:

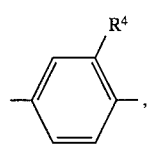

III

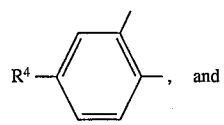

IV

, and

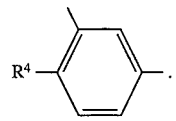

V

12. The compound of claim 9, wherein R is:

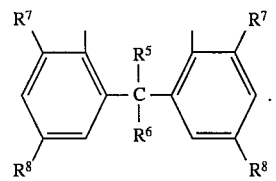

VI

13. The compound of claim 9, wherein R is:

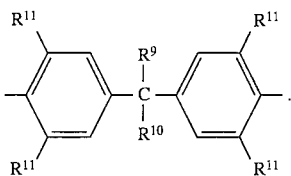

VII

14. The compound of claim 1 wherein $R^1$, $R^2$ and $R^3$ are the same or different and have a Formula Xa:

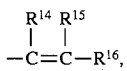

X(a)

wherein $R^{14}$, $R^{15}$ and $R^{16}$ are the same or different and are selected from the group consisting of H and methyl.

15. The compound of claim 1, which has a Formula XIV:

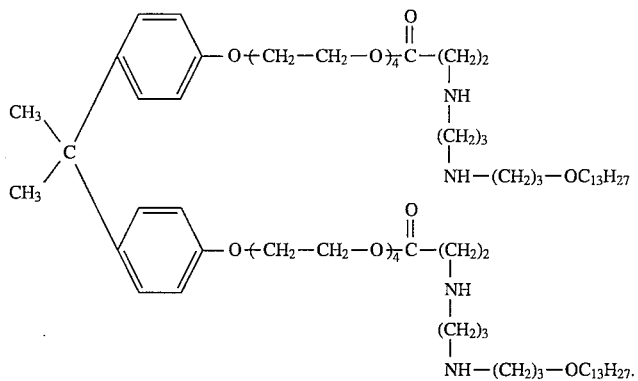

XIV

16. A distillate fuel composition comprising a major amount of a distillate fuel and at least one compound according to claim 1.

17. The distillate fuel composition of claim 16, wherein the distillate fuel is selected from the group consisting of gasoline, diesel fuels, kerosenes, jet fuels, burner fuels, home heating oils and gas oils.

18. A distillate fuel composition comprising a major amount of a gasoline and at least one compound according to claim 9.

19. A distillate fuel composition comprising a major amount of a gasoline and at least one compound according to claim 10.

20. A lubricant composition comprising a major amount of an oil of lubricating viscosity and at least one compound according to claim 1.

21. A lubricant composition comprising a major amount of an oil of lubricating viscosity and at least one compound according to claim 9.

22. A lubricant composition comprising a major amount of an oil of lubricating viscosity and at least one compound according to claim 10.

23. A method for the preparation of a compound according to claim 1 comprising:

a) reacting a poly(oxyalkylene) unsaturated ester with an amine having 1 to 10 nitrogen atoms per molecule by a Michael reaction, the poly(oxyalkylene) unsaturated ester having the following Formula XII:

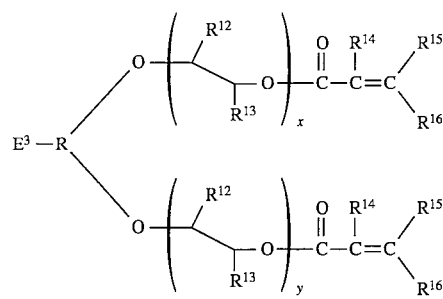

XII $E^3$ being selected from the group consisting of H and a moiety of Formula XII(a):

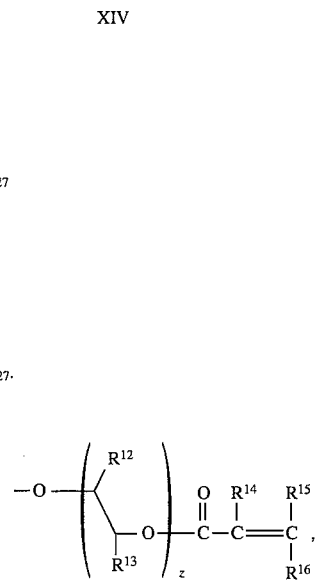

XII(a)

and wherein R is selected from a hydrocarbyl residue of a diol and a hydrocarbyl residue of a triol, $R^{12}$ and $R^{13}$ are independently selected from the group consisting of H, $CH_3$ and $C_2H_5$, $R^{14}$, $R^{15}$ and $R^{16}$ are independently selected from the group consisting of H and $CH_3$, and x, y, and z which may be the same or different, are each an integer of from 1 to 40.

24. The method of claim 23, further comprising making the compound of Formula XII by reacting a poly(oxyalkylene) polyol having the Formula XI:

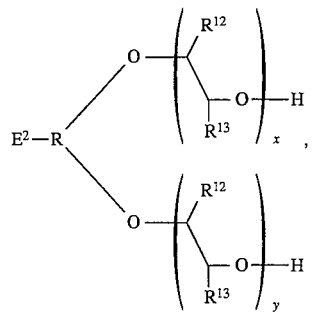

XI wherein $E^2$ is selected from the group consisting of H and a moiety having the Formula XI(a):

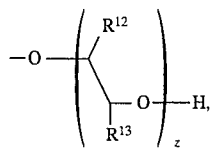  XI(a)

with an unsaturated carboxylic acid having the Formula X:

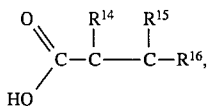  X wherein R is selected from a hydrocarbyl residue of a diol and a hydrocarbyl residue of a triol, $R^{12}$ and $R^{13}$ are independently selected from the group consisting of H, $CH_3$ and $C_2H_5$, $R^{14}$, $R^{15}$ and $R^{16}$ are independently selected from the group consisting of H and $CH_3$, and x, y, and z which may be the same or different, are each an integer of from 1 to 40.

25. The method of claim 24, further comprising making the compound of Formula XI by employing a diol reactant to provide R as a member of the group consisting of a hydrocarbyl moiety of Formula III, IV, V, VI and VII:

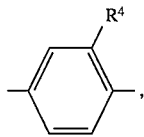  III

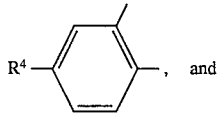  IV
and

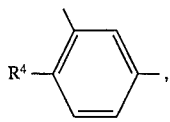  V wherein $R^4$ is selected from the group consisting of H and $C_{1-60}$ alkyls;

$R^5$ and $R^6$ may be the same or different and are selected from the group consisting of H and $C_{1-30}$ alkyls;

each $R^7$ and $R^8$ may be the same or different and is selected from the group consisting of H and $C_{1-60}$ alkyls, $R^9$ and $R^{10}$ may be the same or different and is selected from the group consisting of H and $C_{1-30}$ alkyls, and each $R^{11}$ may be the same or different and is selected from the group consisting of H and $C_{1-60}$ alkyls.

26. A method of operating an internal combustion engine, comprising burning a distillate fuel which contains from about 100 ppm to about 2 weight percent of a compound according to claim 1.

27. A method of reducing the formation of intake valve deposits in an internal combustion engine burning a distillate fuel, comprising operating the engine with a distillate fuel composition containing a compound according to claim 1 in an amount at least sufficient to reduce intake valve deposit formation.

28. A method of reducing the formation of intake valve deposits in an internal combustion engine burning a distillate fuel, comprising operating the engine with a distillate fuel composition containing a compound according to claim 9 in an amount at least sufficient to reduce intake valve deposit formation, wherein the distillate fuel is gasoline.

29. A method of reducing the formation of intake valve deposits in an internal combustion engine burning a distillate fuel, comprising operating the engine with a distillate fuel composition containing a compound according to claim 10 in an amount at least sufficient to reduce intake valve deposit formation, wherein the distillate fuel is gasoline.

30. The method of claim 27, wherein the amount of the compound is at least sufficient to control combustion chamber deposit formation.

31. The method of claim 27, wherein the amount of the compound is at least sufficient to reduce octane requirement increase.

32. A method of dispersing deposits in an internal combustion engine lubricated by an oil of lubricating viscosity, comprising operating the engine with a lubricant comprising a major portion of the oil of lubricating viscosity and a compound according to claim 1.

* * * * *